(12) United States Patent
Jernakoff et al.

(10) Patent No.: US 9,372,145 B2
(45) Date of Patent: Jun. 21, 2016

(54) DEVICES FOR DETERMINING PHOTOPROTECTIVE MATERIALS

(71) Applicant: THE CHEMOURS COMPANY TT LLC, Wilmington, DE (US)

(72) Inventors: Peter Jernakoff, Wilmington, DE (US); Michael Patrick Milone, Pittsgrove, NJ (US); Philipp Martin Niedenzu, Wilmington, DE (US); Cheryl Marie Stancik, Diamondhead, MI (US)

(73) Assignee: THE CHEMOURS COMPANY TT, LLC, Harrisburg, PA (US)

( * ) Notice: Subject to any disclaimer, the term of this patent is extended or adjusted under 35 U.S.C. 154(b) by 0 days.

(21) Appl. No.: 14/395,258

(22) PCT Filed: Apr. 16, 2013

(86) PCT No.: PCT/US2013/036741
§ 371 (c)(1),
(2) Date: Oct. 17, 2014

(87) PCT Pub. No.: WO2013/162947
PCT Pub. Date: Oct. 31, 2013

(65) Prior Publication Data
US 2015/0064068 A1 Mar. 5, 2015

Related U.S. Application Data

(60) Provisional application No. 61/639,318, filed on Apr. 27, 2012.

(51) Int. Cl.
*G01N 17/00* (2006.01)
(52) U.S. Cl.
CPC .................................. *G01N 17/004* (2013.01)

(58) Field of Classification Search
CPC ...................................................... G01N 17/004
USPC .................................................. 422/68.1, 78
See application file for complete search history.

(56) References Cited

U.S. PATENT DOCUMENTS 4,124,301 A * 11/1978 Pocock .......................... 356/432
5,818,599 A * 10/1998 Plavnik et al. ................. 356/440
(Continued)

FOREIGN PATENT DOCUMENTS

EP  1653215 A1  5/2006
FR  2863356 A1  6/2005
(Continued)

OTHER PUBLICATIONS

Palanuk, S.L. et al. (1988). Effect of Agitation, Sampling Location and Protective Films on Light-Induced Riboflavin Loss in Skim Milk. J Food Sci. 53: 436-438.*
(Continued)

*Primary Examiner* — Jill Warden
*Assistant Examiner* — Jacqueline Brazin (57) ABSTRACT

This invention provides methods and apparatus for quantification of photoprotective performance of packaging concepts in an accelerated timeframe. In certain embodiments, the apparatus comprises a light source which provides a light beam that impinges upon a photoprotective material before being transmitted to a sample cell comprising a photosensitive entity, such as a photosensitive nutrient. In certain embodiments, the apparatus and methods can be used to generate models for the prediction of photoprotective performance values of untested materials based upon some other known qualitative or quantitative property.

10 Claims, 7 Drawing Sheets

(56) References Cited

U.S. PATENT DOCUMENTS

| | | |
|---|---|---|
| 2011/0103423 A1 | 5/2011 | Hsu et al. |
| 2011/0170093 A1 | 7/2011 | Inoue et al. |

FOREIGN PATENT DOCUMENTS

| | | | |
|---|---|---|---|
| WO | 2009136861 A1 | | 11/2009 |
| WO | WO 2009/136861 | * | 11/2009 |

OTHER PUBLICATIONS

Atkins ; Table 26.1 Photochemical Processes. Physical Chemistry, 5th Edition; Freeman: New York, 1994; 908.

Kline et al., Light Wavelength Effects on a Lutein-Fortified Model Colloidal Beverage. J. Agric. Food Chem. 2011, 59, 7203-7210.

Webster et al., Int. Dairy Journal. 2011, 21, 305-311.

Webster et al., Controlling Light Oxidation Flavor in Milk by Blocking Riboflavin Excitation Wavelengths by Interference. J. Food Sci. 2009, 74, S390-S398.

Palanuk et al.; Effect of agitation, sampling location and protective films on light-induced riboflavin loss in skim milk. J. Food Sci.1988, 53, 436-438.

Cladman et al.; Shelf-life of Milk Packaged in Plastic Containers With and Without Treatment to Reduce Light Transmission. Int. Dairy Journal. 1998, 8, 629-636).

Saffert et al.; Effect of Package Light Transmittance on the Vitamin Content of Pasteurized Whole Milk. Packag. Technol. Sci. 2006, 19, 211-218.

Min et al.; Chemistry and Reaction of Singlet Oxygen in Foods. CRFSFS. 2002, 1, 58-72.

Turhan et al., A simple method for determining light transmittance of polymer films used for packaging foods Hacettepe University, Food Engineering Department, Beytepe, Ankara 06532, Turkey Polymer International ( Polym. Int. ) ( United Kingdom ) 2001 50/10 (1138-1142).

International Search Report, PCT/US2013/036741, mailed Jul. 18, 2013.

Coltro et al., "Plastic packages for personal care products—Evaluation of light barrier properties.", Polimeros: Ciencia E Tecnologia, vol. 17, No. 1, Jan. 1, 2007.

Ahmad et al., International Journal of Pharmaceutics (2004), 280(1-2), 199-208.

Title: Plastic Packaging for Beer Source: PETplanet insider ; 9, No. 8, Aug. 25, 2008, p. 35-36.

Title: Let There Be Light Source: Plastic Packaging Innovation News ; 1, No. 24, Dec. 14, 2005, p. 5 ISSN: 1478-7059.

Korman et al., Simple procedure for assessing the protective effect of transparent polymer films used for packaging foods containing light-sensitive nutrients Polymer International ( Polym Int ) 1991 25/3 (163-166).

Saffert Effect of Package Light Transmittance on Vitamin Content of Milk. Part 2: UHT Whole Milk. Packag. Technol. Sci. 2008, 21, 47-55.

Lu, et al. Effect of light-banier property of packaging film on the photo-oxidation and shelf life of cookies based on accelerated tests. Packaging Technology and Science 22, 107-113 2009 ISSN No. 0894-3214.

* cited by examiner

DEVICES FOR DETERMINING PHOTOPROTECTIVE MATERIALS

FIELD OF THE INVENTION

This invention relates to the field of packaging technology, more specifically to methods and apparatus for testing materials for photoprotective properties.

BACKGROUND

It is well understood that certain compounds and nutrients contained within packages can be negatively impacted by exposure to light. Many different chemical and physical changes can result to molecular species as either a direct or indirect result of exposure to light, which can collectively be defined as photochemical processes. As described in Atkins, photochemical processes can include primary absorption, physical processes (e.g., fluorescence, collision-induced emission, stimulated emission, intersystem crossing, phosphorescence, internal conversion, singlet electronic energy transfer, energy pooling, triplet electronic energy transfer, triplet-triplet absorption), ionization (e.g., Penning ionization, dissociative ionization, collisional ionization, associative ionization), or chemical processes (e.g., disassociation or degradation, addition or insertion, abstraction or fragmentation, isomerization, dissociative excitation) (Atkins, P. W.; Table 26.1 Photochemical Processes. *Physical Chemistry, 5th Edition*; Freeman: New York, 1994; 908). As one example, light can cause excitation of photosensitizer species (e.g., riboflavin in dairy food products) that can then subsequently react with other species present (e.g., oxygen, lipids) to induce changes, including degradation of valuable products (e.g., nutrients in food products) and evolution of species that can adjust the quality of the product (e.g., off-odors in food products).

As such, there is an art-recognized need to provide packaging with sufficient photoprotective properties to allow the protection of the package content(s). In certain studies, actual packaging systems and photochemical reactors have been used as a means to provide an indication of photoprotective performance of packaging concepts. However, generally these studies allow for the evaluation of only a single packaging concept and do not demonstrate sufficiently robust methods to allow for relative comparisons between experiments, nor the capability to produce performance design models based on the results.

For instance, the work of Kline et al. (Kline, M. A.; Duncan, S. E.; Bianchi, L. M.; Eigel, W. N., III; O'Keefe, S. F.; Light Wavelength Effects on a Lutein-Fortified Model Colloidal Beverage. *J. Agric. Food Chem.* 2011, 59, 7203-7210) studying the light effects on a model colloidal beverage acknowledges the challenge to make relative comparisons between experimental conditions with their method due to changes in light intensity; however, they fail to demonstrate a suitable solution. Similarly, Webster et al. (Webster, J. B.; Duncan, S. E.; Marcy, J. E.; O'Keefe, S. F.; Effect of narrow wavelength bands of light on the production of volatile and aroma-active compounds in ultra high temperature treated milk. *Int. Dairy Journal.* 2011, 21, 305-311), studying the effects of light on milk, acknowledge the inability to make direct comparisons between all experiments due to differences in light energy output as a limitation of their capability (see also Webster, J. B.; Duncan, S. E.; Marcy, J. E.; O'Keefe, S. F.; Controlling Light Oxidation Flavor in Milk by Blocking Riboflavin Excitation Wavelengths by Interference. *J. Food Sci.* 2009, 74, S390-S398). As another example, in a study by Palanuk (Palanuk, S. L.; Warthesen, J. J.; Smith, D. E.; Effect of agitation, sampling location and protective films on light-induced riboflavin loss in skim milk. *J. Food Sci.* 1988, 53, 436-438), sampling location was shown to influence the results in studies of the effects of light on riboflavin in skim milk.

Additionally, studies in this field frequently require an extended testing period, such as days or weeks. For instance, Cladman (Cladman, W.; Scheffer, S.; Goodrich, N.; Griffiths, M. W.; Shelf-life of Milk Packaged in Plastic Containers With and Without Treatment to Reduce Light Transmission. *Int. Dairy Journal.* 1998, 8, 629-636) performed a study on photoprotective properties of materials that required a twenty day period to expose the samples. As another example, while Saffert et al. report two studies (Saffert, A.; Pieper, G.; Jetten, J.; Effect of Package Light Transmittance on the Vitamin Content of Pasteurized Whole Milk. *Packag. Technol. Sci.* 2006, 19, 211-218; Saffert, A.; Pieper, G.; Jetten, J.; Effect of Package Light Transmittance on Vitamin Content of Milk. Part 2: UHT Whole Milk. *Packag. Technol. Sci.* 2008, 21, 47-55) that explore package performance related to retaining nutrients in milk, they conducted the study under conditions that required days of exposure.

Given the above, a robust scientific method to rapidly quantify photoprotective performance of packaging concepts in a way that allows relative comparisons between the packaging concepts and is relevant to the conditions used for such packaging concepts in their targeted real-world applications is needed. These methods are needed to allow for the creation of performance design models for packaging concepts, and to allow for efficient design of photoprotective packages that achieve the required balance of performance attributes for a given package cost, weight, material usage, or other design requirements.

SUMMARY OF INVENTION

In one aspect, the present invention relates to a method for predicting the photoprotective performance of a material, the method comprising: (a) providing a sample comprising one or more photosensitive entities; (b) providing a cell having controlled optical properties to contain the sample at a predetermined temperature between about −20° C. and about 100° C.; (c) providing a light source that generates a light beam with a spectral signature between about 290 and about 1000 nm and an intensity between about 0.01 and about 5 W/cm$^2$; (d) placing the photosensitive entity into the cell, rendering a sample cell; (e) placing a first test material between the light source and the sample cell, rendering a shielded sample cell, wherein the light beam impinges upon the first test material and any penetrating light impinges upon the sample cell, and wherein the first test material comprises a known quantitative or qualitative property; (f) exposing the shielded sample cell to one or more light beam intensities for one or more durations; (g) measuring the changes to the one or more photosensitive entities contained within the shielded sample cell at one or more durations to generate data points either by studying the sample while it is contained within the exposure cell or by removing a sample for measurement by external methods; (h) using the data points to determine a photoprotective performance value of the first test material; (i) repeating steps (a)-(h) with one or more additional test materials to generate one or more additional photoprotective performance values; (j) utilizing the two or more photoprotective performance values to generate a model for a class of materials with the known qualitative or quantitative property that predicts the photoprotective performance of an untested material within the same class based upon the known quantitative or qualitative property of the untested material.

In certain embodiments, the quantitative or qualitative property comprises one or more of the following: whiteness index ASTM E313; brightness index ASTM D985; CIE (1976) L*a*b* tri-stimulus data ASTM designation of E313-10, D2244, E 1347, E1349, E1477, E2214, E284, E308, E805, E991, E1331, E275, D2616, D2745, D3134, D3964, D4877, D6290; DuPont Appearance Analyzer data; Diffuse Brightness of Paper and Paperboard (d/0) ASTM D2470; Standard test for haze for plastics ASTM D1003; Brightness, Directional (TAPPI) (T452); Brightness Directional; Brightness, Diffuse (T525); Brightness with Color (Diffuse (Micro TB1C) or Directional/TAPPI (MicroS-5)); Printing & calculated TAPPI Opacity, Scattering & Absorption Coefficients, Sheet Brightness (T519); Directional/TAPPI Opacity, Scattering Coefficient, Absorption Coefficient (T425); T/dyne Micro TB-1C: Diffuse brightness, opacity, color, color difference, ASTM Index, & tristimulus; T/dyne Micro S-5 BOC: Dir/TAPPI brightness, opacity, color, color difference, ASTM Index, & tristimulus; Color, Hunter or CIE L*A*B* (State Directional or Diffuse Values), opacifying agent composition(s), and/or opacifying agent(s) loading as a design parameter.

In additional embodiments, the predictive models are used to facilitate the design of packages that provide photoprotection specific for the package contents. In other embodiments, the predictive models are used to assess sustainability metrics for a package design. In certain particular examples, the package contents include food, beverages, drugs, pharmaceuticals, and/or other nutrient-containing products.

In certain embodiments, the method further comprises correlating the changes to the one or more photosensitive entities in step (g) with one or more sensory evaluation criteria values and utilizing said predicted photoprotective performance to further predict one or more sensory evaluation criteria values of an untested material. Sensory evaluations comprise human evaluation of one or more of the following criteria: taste, texture, odor, or appearance.

In further embodiments, the sample is maintained under one or both of controlled atmosphere conditions and under agitation, the exterior surface of the sample cell is maintained free from condensate, and/or the light beam is collimated.

In some embodiments, the one or more photosensitive entities are constituents of food, beverages, drugs, pharmaceuticals, or other nutrient-containing products. In other embodiments, the sample comprises one or more photosensitive entities selected from natural and synthetic food additives, dyes, and pigments; chlorophyll; myoglobin, oxymyoglobin, and other hemeproteins; water and fat soluble essential nutrients, minerals, and vitamins; food components containing fatty acids; oils; proteins; pharmaceutical compounds; personal care and cosmetic formulation compounds and components; household chemicals and their components; and agricultural chemicals and their components. In additional embodiments, the sample comprises one or more photosensitive entities selected from 2, 3, 4, 5, 6, 7, 8, 9, 10, or more of the given classes.

In further embodiments, the measuring comprises a test method selected from the group consisting of HPLC (high performance liquid chromatography), GC (gas chromatography), IR (infrared) spectroscopy, NMR (nuclear magnetic resonance) spectroscopy, UV-VIS (ultra-violet, visible) spectroscopy, MS (mass spectrometry) coupled with other techniques (e.g., GC-MS and LC-MS), fluorescence spectroscopy, ion chromatography, thin layer chromatography (TLC), analytical wet chemistry, and/or electrochemical analysis (e.g., polarography, voltammetry). In particular embodiments, the analytical method is HPLC (high performance liquid chromatography) or GC (gas chromatography).

In another aspect, the present invention relates to a device for quantifying the photoprotective performance of a material, the device comprising: (a) a sample supply and control apparatus comprising: (I) a cell having controlled optical properties, the cell capable of containing a sample comprising one or more photosensitive entities; (II) a sample temperature sensor for monitoring the temperature of the sample within the cell; (III) a temperature control for maintaining the cell at a specified temperature between about −20° C. and about 100° C.; (IV) a dry air supply for delivering low-humidity air to one or more exposed surfaces of the cell; and (V) an agitator for maintaining sample homogeneity within the cell; (b) a light generation and control apparatus comprising: (I) a light source, wherein the light source generates a light beam with a spectral signature between about 290 and about 1000 nm and an integrated intensity between about 0.01 and about 5 W/cm$^2$; (II) a light beam collimating lens; (III) an infrared filter; (IV) a shutter; and (V) an iris; and (c) a test material holder positioned between the light generation and control apparatus and the sample supply and control apparatus such that, when a test material is placed in the test material holder, the light beam impinges upon the test material and any penetrating light impinges upon the cell.

In certain embodiments, the agitator comprises a magnetic stir bar within the cell and a magnetic stirring motor positioned below the cell. In other embodiments, the sample supply and control apparatus further comprises an atmosphere control and monitoring apparatus within the cell, wherein the atmosphere control and monitoring apparatus comprises a gas supply device and an oxygen sensor. In still further embodiments, the light generation and control apparatus further comprises a spectral filter.

DETAILED DESCRIPTION

It is to be understood that this invention is not limited to particular embodiments, which can, of course, vary. It is also to be understood that the terminology used herein is for the purpose of describing particular embodiments only, and is not intended to be limiting. Further, all publications referred to herein are incorporated by reference herein for the purpose cited to the same extent as if each was specifically and individually indicated to be incorporated by reference herein.

As used in this specification and the appended claims, terms in the singular and the singular forms "a," "an," and "the," for example, include plural referents unless the content clearly dictates otherwise. Thus, for example, reference to "photosensitive entity," "the photosensitive entity," or "a photosensitive entity" also includes a plurality of photosensitive entities. Use of the term "a photosensitive entity" also includes, as a practical matter, many molecules of that photosensitive entity.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a sample comprising a photosensitive entity may contain additional photosensitive entities or other components, such as other non-photosensitive nutrients. Additionally, the term "comprising" is intended to include examples encompassed by the terms "consisting essentially of" and "consisting of." Similarly, the term "consisting essentially of" is intended to include examples encompassed by the term "consisting of."

The present invention relates to devices and methods useful for determining and/or quantifying photoprotective properties of a material, and for making meaningful comparisons between such properties, by quantifying the light-induced change or degradation of one or more photosensitive entities. In another embodiment, the method involves correlating a photoprotective performance value with another known quantitative or qualitative property of a material, such as the material's TAPPI Opacity or titanium dioxide content, to produce a predictive or correlative model. In another embodiment, the method further involves using the predictive or correlative model to assign a predicted photoprotective performance value to an untested material within the same material class based on the correlative property value.

The present apparatus allows for the accelerated testing of photoprotective properties. In certain embodiments, a test can be performed in a matter of hours while simulating the light exposure of several weeks under commercial food storage conditions. This method can thus be considered a high throughput screening method, as the testing rates can be accelerated over 100 times. In certain embodiments, the method and apparatus can be used to determine an optimum amount of light-protective agent, such as $TiO_2$, to include in a packaging material for photo-protection.

In certain other embodiments, this method can be useful to predict the results of sensory evaluations for a certain package concept, thereby avoiding the time and resources required to actually conduct sensory evaluation research on that package concept. Typically sensory evaluation research with human subject appraisers requires a large number of panelists and product assessments due to the limitations of the panelists' ability to accurately and precisely detect differences in sensory qualities of a product. As such, this type of evaluation of a packaging concept is generally both time consuming and costly. By using the methods of the present invention to predict the results of such a sensory evaluation, the present invention allows for sensory evaluation results to be obtained in an accelerated timeframe and at a decreased cost.

The method and apparatus also provide a means to compare not-in-kind protective packaging solutions. For example, polymeric packaging films can be compared to paperboard.

FIGS. 1 and 2A-2C illustrate one possible embodiment of an apparatus of the present invention which is useful in the disclosed methods. The individual components of the overall apparatus are contained within an enclosure 60, which is generally light blocking with regard to the spectra being analyzed during an experiment. To maintain proper atmospheric conditions (temperature, humidity, etc.) within the enclosure, the enclosure 60 possesses an exhaust fan and fan trunk 58, which allows the air within enclosure 60 to be cycled at a desired interval and/or rate.

Figure 1:
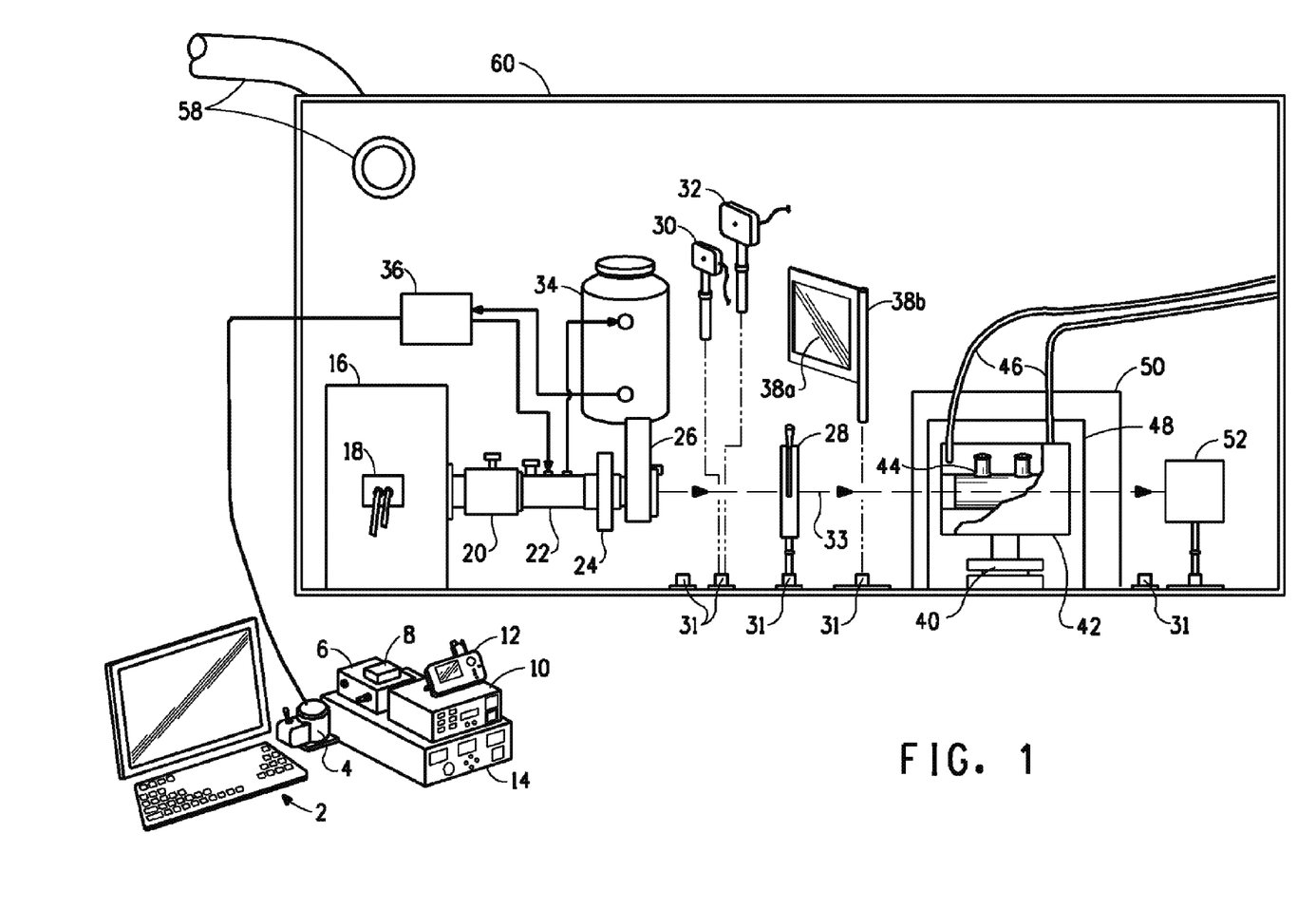
FIG. 1 illustrates an embodiment of an apparatus useful in the present invention.

Within enclosure 60, a light source, such as a lamp (not shown) contained within lamp housing 16, is connected via appropriate electrical connections (not shown) to a light source power supply 14, which in turn is connected via appropriate electrical connections (not shown) to a lamp controller 10.

The light source can be any suitable light source to produce the desired light intensity, stability, and spectral characteristics. Depending upon the needs of the experiment, light sources employed may include incandescent light sources, fluorescent light sources, arc discharge lamps, LEDs (light emitting diodes), and/or laser light sources. For example, these light sources include but are not limited to carbon arc, mercury vapor, xenon arc, tungsten filament, or halogen bulbs. In one particular embodiment, the light source is a xenon arc lamp.

In certain embodiments, the light source is capable of providing an intensity of between about 0.001 $W/cm^2$ and about 5 $W/cm^2$. In other embodiments, the light source is capable of providing an intensity of at least about 0.001 $W/cm^2$, 0.005 $W/cm^2$, 0.007 $W/cm^2$, 0.01 $W/cm^2$, 0.05 $W/cm^2$, 0.1 $W/cm^2$, 1 $W/cm^2$, 2.5 $W/cm^2$, or 5 $W/cm^2$. In further embodiments, the light source is capable of providing an intensity of not more than about 0.001 $W/cm^2$, 0.005 $W/cm^2$, 0.007 $W/cm^2$, 0.01 $W/cm^2$, 0.05 $W/cm^2$, 0.1 $W/cm^2$, 1 $W/cm^2$, 2.5 $W/cm^2$, or 5 $W/cm^2$. In further embodiments, the light source is capable of providing an intensity between about 0.005 $W/cm^2$ and about 4 $W/cm^2$, between about 0.007 $W/cm^2$ and about 3 $W/cm^2$, between about 0.01 $W/cm^2$ and about 2.5 $W/cm^2$, between about 0.05 $W/cm^2$ and about 2 $W/cm^2$, or between about 0.1 $W/cm^2$ and about 1 $W/cm^2$.

In other embodiments, the light source is capable of producing light with a spectral signature of about 200 nm to about 2000 nm. In other embodiments, the light source is capable of providing light at a wavelength of at least about 200 nm, 220 nm, 240 nm, 260 nm, 280 nm, 290 nm, 300 nm, 350 nm, 400 nm, 450 nm, 500 nm, 550 nm, 600 nm, 650 nm, 700 nm, 750 nm, 800, nm, 900 nm, 1000 nm, 1250 nm, 1500 nm, 1750 nm, or 2000 nm. In further embodiments, the light source is capable of providing light at a wavelength of not more than about 200 nm, 220 nm, 240 nm, 260 nm, 280 nm, 290 nm, 300 nm, 350 nm, 400 nm, 450 nm, 500 nm, 550 nm, 600 nm, 650 nm, 700 nm, 750 nm, 800, nm, 900 nm, 1000 nm, 1250 nm, 1500 nm, 1750 nm, or 2000 nm. In still further embodiments, the light source is capable of providing a spectral signature of about 220 nm to about 1750 nm, about 240 to about 1500 nm, about 260 to about 1250 nm, about 290 to about 1000 nm, about 200 to about 400 nm, about 350 to about 750 nm, or above about 750 nm.

In certain embodiments, the intensity and/or spectral characteristics of the light source are controlled and/or modified by one or more of a lens, an infrared filter, and a spectral filter. In one particular embodiment, the light from a lamp within lamp housing 16 travels through a collimating lens assembly 20, then through an infrared filter 22, which is a water-based infrared filter attached to water reservoir 34 and water pump 36, the flow volume of which is controlled by a pump flow controller 4 to which water pump 36 is attached via appropriate electrical connections. The collimated and infrared-filtered light then travels through an optical filter holder 24, which can optionally contain an optical filter or filters to attenuate the light beam or portions thereof. Though the lens, infrared filter, and spectral filter(s) are shown in a particular order in FIGS. 1 and 2a, this is not to be taken as an indication that all of these components are required, nor that the indicated order is required. These components could be used in any desired order and/or in any desired combination, including employing none of them in the apparatus and method of the invention.

In certain embodiments, within enclosure 60, a light source, such as a lamp (not shown) contained within lamp housing 16, is connected via appropriate electrical connections (not shown) to a light source power supply 14, which in turn is connected via appropriate electrical connections (not shown) to a lamp controller 10. Lamp feedback monitor 18 is electrically connected to the lamp controller 10. The lamp feedback monitor 18 communicates with the lamp controller 10 which in turn communicates with the light source power supply 14 to adjust the amount of power provided to the light source and/or in order to adjust the intensity of the light emanating from the light source.

In one embodiment, to ensure that the light beam possesses the proper intensity, a light power density sensor 30 can be located, for instance removably located, within one of a plurality of holders 31 along light path 33. The light power density sensor 30 is attached via appropriate connections (not shown) to the optical energy meter 12. Light power density sensor 30 can be inserted into holder 31, so that a discrete intensity reading can be taken, for instance, prior to the initiation of an experiment and again after the termination of an experiment and/or at times during an experiment. This would allow the intensity of the light beam to be tested both before and after an experiment so that the user can ensure that the power intensity was correctly set and did not significantly increase or decrease throughout the experiment.

In other embodiments, in order to ensure that the light beam possesses the proper spectral characteristics, a spectrometer sensor 32 can be removably located within one of a plurality of holders 31 along light path 33. The spectrometer sensor 32 is attached via appropriate connections (not shown) to a spectrometer 8. Spectrometer sensor 32 can be inserted into holder 31, so that a discrete spectrometry reading can be taken, for instance, prior to the initiation of an experiment and again after the termination of an experiment. This would allow the spectral characteristics of the light beam to be tested before and after an experiment so that the user can ensure that the spectral characteristics were as desired and stable in the time frame of the experiment.

Light exposure initiation and cessation during operation of the apparatus or method can be controlled, for example, by a shutter mechanism 26, the operation of which is controlled by a shutter controller 6, to which it is attached via appropriate connections (not shown). Further, the cross sectional area of the light beam impinging upon a test material and/or sample can be adjusted by an iris 28 located within one of the plurality of holders 31, which can be opened and closed as needed to produce a light beam of the desired diameter. Again, though these components are illustrated in FIG. 1, this should not be taken as an indication that one or all of them is required. For instance, the apparatus could be operated without a shutter by simply controlling initiation of the light beam through the lamp controller 10 and/or light source power supply 14. Similarly, the size of the light beam could be alternatively controlled, for example, through the collimating lens 20.

Figure 2A:
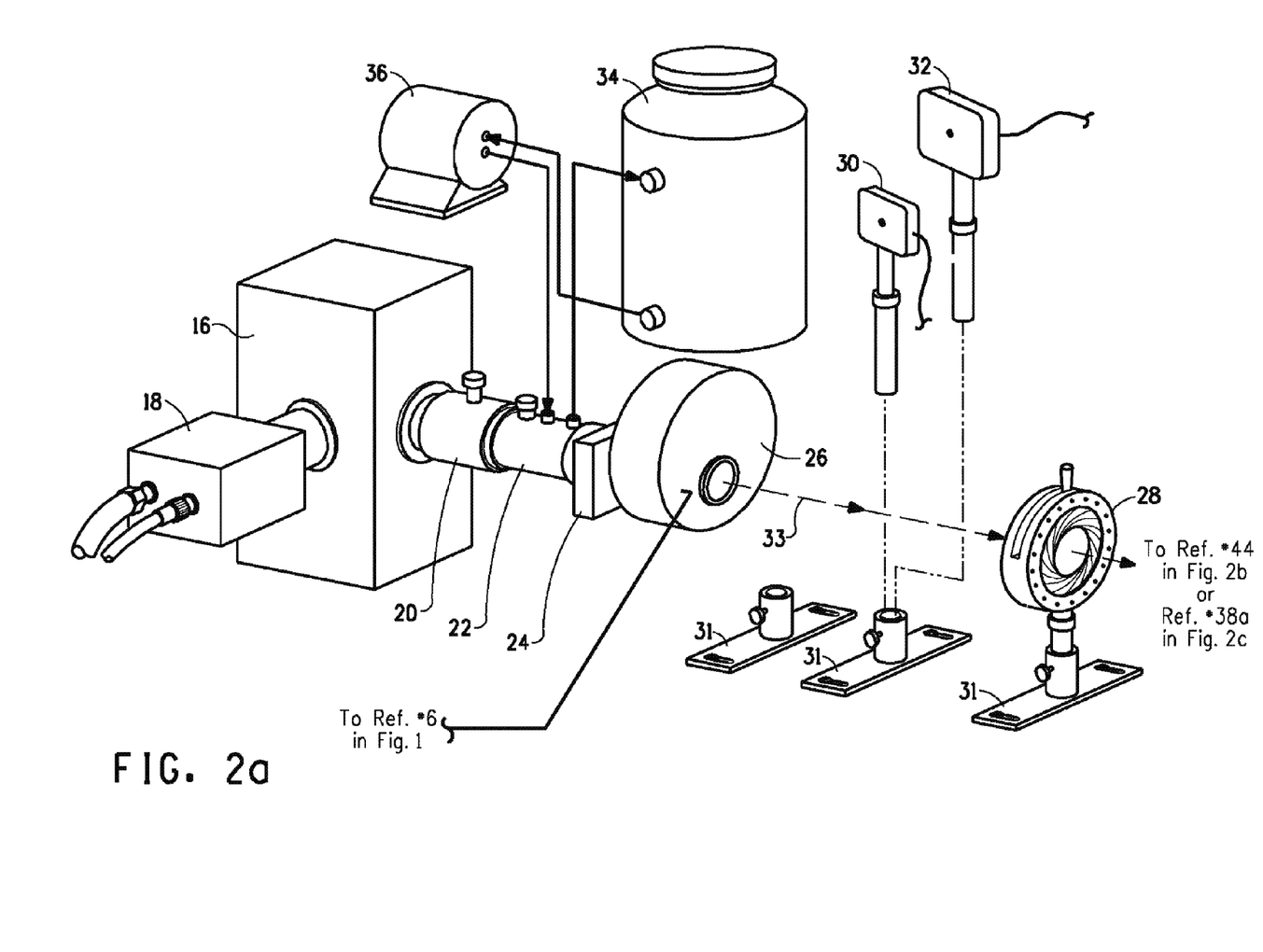
FIGS. 2A-2C illustrate more detailed views of particular elements of the illustrative embodiment of FIG. 1.
Figure 2B:
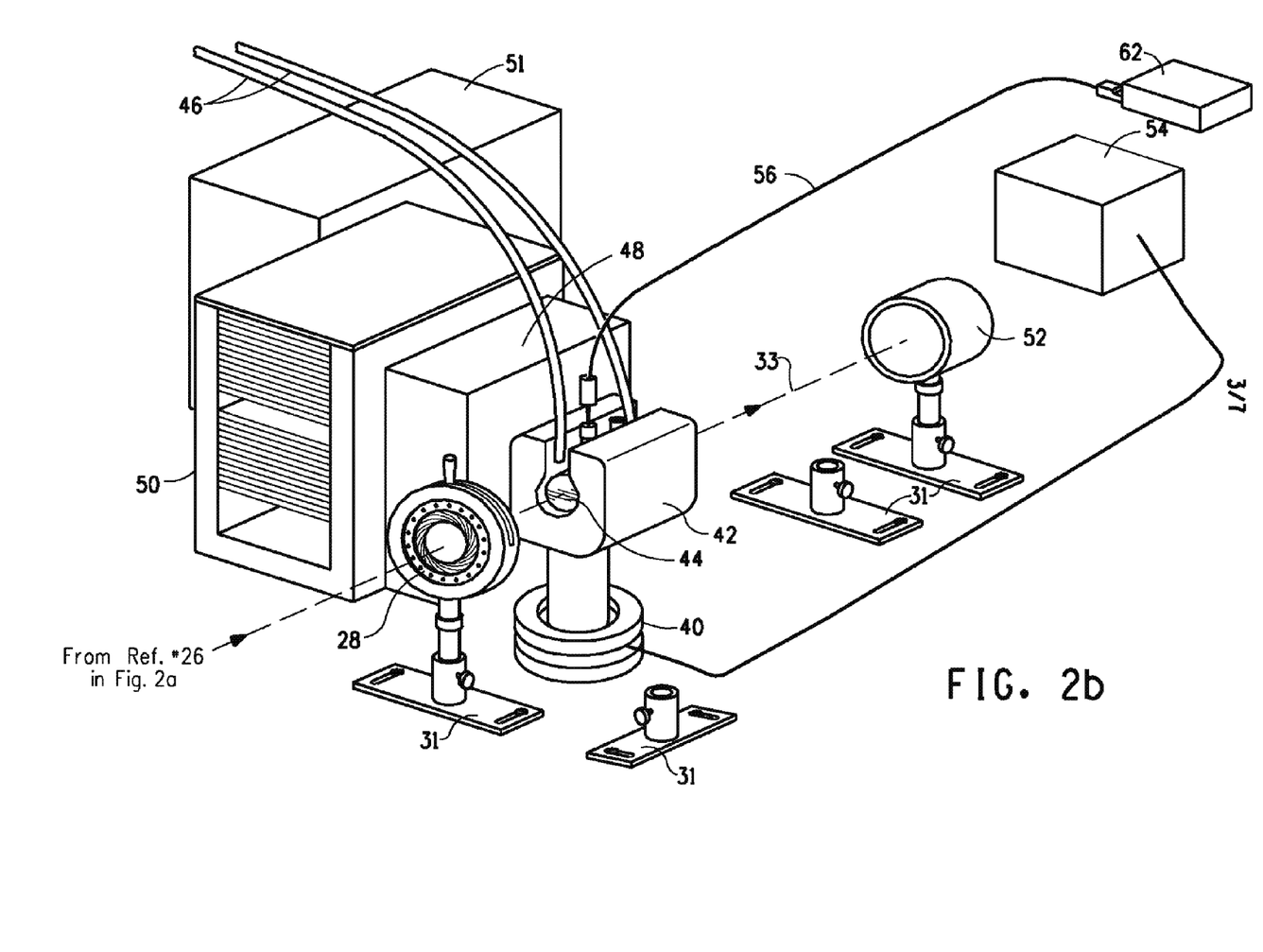
Figure 2C:
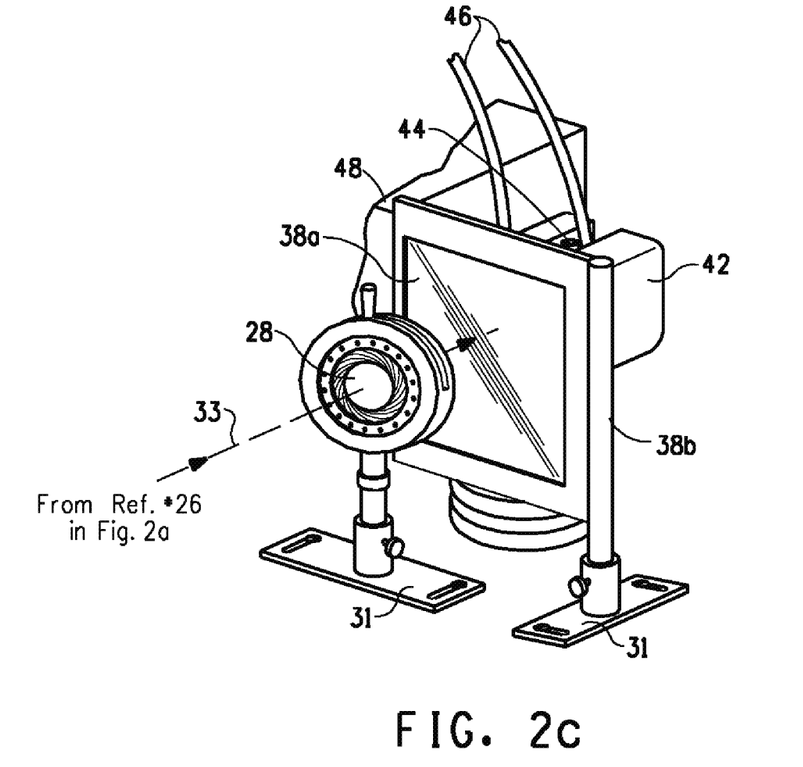

Looking at FIGS. 1, 2b, and 2c, after passing through the iris 28, the light beam will impinge upon a test material 38a, which is held in place by material holder 38b, which is in turn located within one of the plurality of holders 31. The test material 38a can be a material with certain known qualitative or quantitative properties, such as TAPPI Opacity or titanium dioxide content, or can be a completely unknown material. Further, the test material 38a can be any material suitable for use as a packaging material or photoprotective material. Such materials include plastics (polymeric materials, e.g., low density polyethylene), glass, metal (e.g., cans, foils, or metalized layers), cellulosic materials (e.g., paper, paperboard), or combinations thereof in forms such as films (e.g., plastic wraps), sheets (e.g., papers), bags, sleeves, pouches, or rigid structures (e.g., bottles). These materials may also contain additives (e.g., pigments, printing inks, antioxidants) to provide additional appearance attributes or functionalities to the material. In certain embodiments, the material contains titanium dioxide. Materials tested could comprise an actual package, a portion of a packaging material, or a prototype of a portion of a packaging system including films, foils, plaques from rigid parts, papers, and laminated or composite structures of these materials.

The light transmitted by the test material 38a will in turn impinge upon the sample cell 44, which will be held in place during the experimental run by sample cell holder 42, which optionally can be insulated so that it retains temperature more efficiently and effectively. Sample cell holder 42 is in direct contact with heat transfer block 48, which is attached to thermoelectric device 50, under the control of thermoelectric controller 51. Thermoelectric device 50 can be either a heater or cooler, or a device that is capable of both heating and cooling. In certain examples, thermoelectric device 50 is a piezoelectric cooling unit. During operation, thermoelectric controller 51 directs a temperature set point for thermoelectric device 50. Through heat transfer block 48, the temperature gradient (cold or heat) generated by thermoelectric device 50 is transferred to sample cell holder 42. This allows the temperature within sample cell 44 to be maintained at a fixed temperature throughout an experimental run. Optionally, a heat transfer compound can be used to facilitate heat transfer between the sample cell 44 and the sample cell holder 42. In certain embodiments, the temperature can be set at a temperature between about −20° C. and about 100° C. In other embodiments, the temperature can be set at a temperature of at least about −20° C., −10° C., −5° C., −2° C., 0° C., 1° C., 2° C., 3° C., 4° C., 5° C., 6° C., 7° C., 8° C., 10° C., 25° C., 50° C., or 100° C. In further embodiments, the temperature can be set at a temperature of not more than about −20° C., −10° C., −5° C., −2° C., 0° C., 1° C., 2° C., 3° C., 4° C., 5° C., 6° C., 7° C., 8° C., 10° C., 25° C., 50° C., or 100° C. In still further embodiments, the temperature can be set at between about −10° C. and about 50° C., about −5° C. and about 25° C., about −2° C. and about 10° C., about 0° C. and about 8° C., about 1° C. and about 7° C., about 2° C. and about 6° C., about 3° C. and about 5° C. In certain other embodiments, the temperature is set at about 4° C.

Sample cell 44 can comprise any suitable material and shape such that it possesses the desired optical characteristics. Preferably, sample cell 44 is optically transparent in the spectral range being investigated during the experiment. In certain embodiments, sample cell 44 is made of quartz. In certain embodiments, such as those shown in FIGS. 1 and 3, sample cell 44 can be substantially flat on one end, thereby allowing the light to impinge upon the sample cell at an angle that is substantially perpendicular to the flat end of the sample cell 44, which can be a desirable optical situation. In certain embodiments, such as those shown in FIGS. 1 and 3, sample cell 44 can also be equipped with one or more access ports 43 to allow test samples, additives, or gases to be added or withdrawn from the cell and/or to allow sample cell thermocouple 56 or other probes or sensors to be inserted into sample cell 44 during an experimental run. Sample cell thermocouple 56 is in turn attached, via appropriate connections, to temperature meter 62. This can allow the temperature of the sample to be monitored and/or controlled throughout an experimental run. In certain embodiments, thermocouple 56 and/or temperature meter 62 is placed in communication with thermoelectric controller 51 such that the temperature can be automatically adjusted throughout an experimental run to maintain the sample at the desired temperature.

Figure 3:
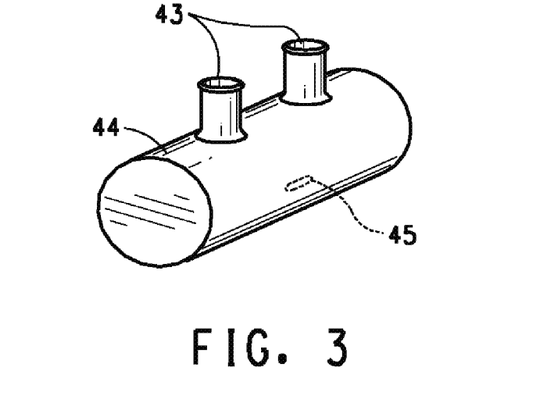
FIG. 3 illustrates an embodiment of a sample cell useful in the present invention.

Further, access ports 43 could allow for an optional gas delivery tube and/or atmospheric sensor (not shown) to be inserted into the sample cell during an experimental run for monitoring and/or controlling the atmospheric conditions within sample cell 44 throughout the experimental run. Additionally, as illustrated in FIGS. 1 and 2b, directly below insulated sample cell holder 42 is a magnetic stirring motor 40, which is attached via appropriate connections to a magnetic stirrer speed controller 54. As shown in FIG. 3, this allows a magnetic stir bar 45 to be located within sample cell 44 during an experimental run so that the magnetic stirring motor can effectuate agitation of the sample at a desired speed throughout an experimental run, thereby ensuring substantial sample homogeneity.

Figure 4:
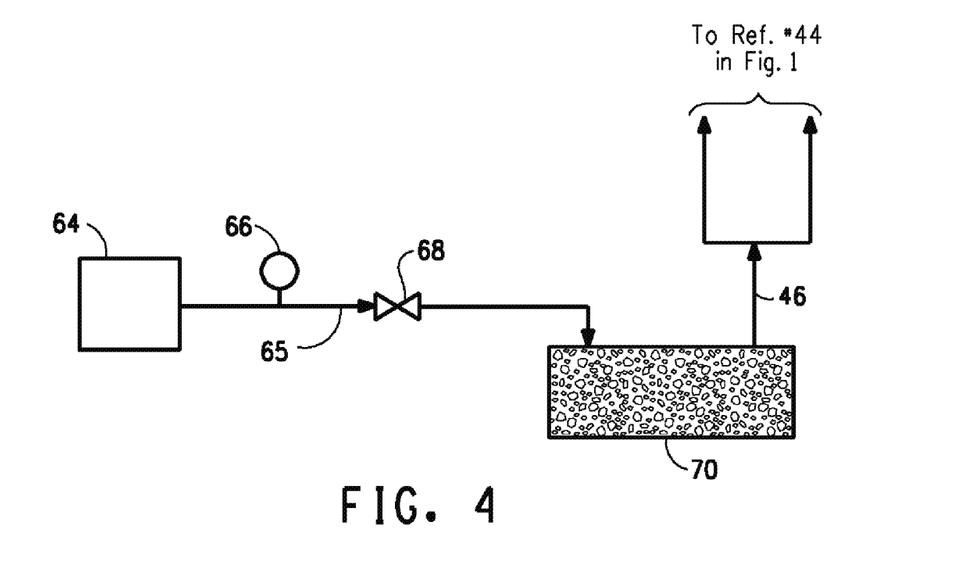
FIG. 4 illustrates an embodiment of a dry-air supply apparatus useful in the present invention.

As shown in FIG. 1, in certain embodiments, dry air, meaning air with relatively low humidity, can be supplied to the front and/or rear faces of sample cell 44 via delivery tubes 46 in order to prevent or reduce condensation forming on the sample cell. As used herein, the term "air" means atmospheric air or any other suitable gas, such as gaseous nitrogen. With reference to FIG. 4, air is supplied from supply 64, via feed line 65, to pressure regulator 66. The air then continues through feed line 65 to flow valve 68 before traveling through drying chamber 70. Drying chamber 70 can be any suitable type of apparatus for reducing humidity in air. For instance, in certain embodiments, drying chamber 70 can be a polycarbonate tube filled with a desiccant, such as "Drierite" desiccant. The reduced-humidity air then exits the drying chamber and travels via delivery tubes 46 to the faces of sample cell 44, where it is released.

Any light that passes completely through sample cell 44 will eventually impinge upon beam stop 52, which is constructed in such a way that captures substantially all remaining light without allowing any significant portion of the light to reflect back toward the sample cell.

In certain embodiments, one or more of the components of the overall apparatus may be controlled or monitored by computer 2. This can include one or more of light source power supply 14, lamp controller 10, pump flow controller 4, water pump 36, lamp output feedback detector 18, optical energy meter 12, shutter mechanism 26, shutter controller 6, iris 28, spectrometer 8, thermocouple 56, temperature meter 62, thermoelectric controller 51, magnetic stirrer speed controller 54, oxygen sensor (not shown), air supply 64, or pressure regulator 66.

During operation of the apparatus disclosed herein, a test material 38a is placed within the material holder 38b and one or more photosensitive entities is placed in the sample cell. Examples of test materials that can be investigated using the present invention include plastics (polymeric materials, e.g., low density polyethylene), glass, metal (e.g., cans, foils, or metalized layers), cellulosic materials (e.g., paper, paperboard), or combinations thereof in forms such as films (e.g., plastic wraps), sheets (e.g., papers), bags, sleeves, pouches, or rigid structures (e.g., bottles). These materials may also contain additives (e.g., pigments, printing inks, antioxidants) to provide additional appearance attributes or functionalities to the material. Packaging concepts would be comprised of these same materials and could comprise an actual package, a portion of a packaging material, or a prototype of a portion of a packaging system including films, foils, plaques from rigid parts, papers, and laminated or composite structures of these materials.

In certain embodiments, the photosensitive entity is a photosensitive nutrient. In particular embodiments, the photosensitive entity is selected from:
  i. natural and synthetic food additives, dyes, and pigments (e.g., curcumin, erythrosine);
  ii. chlorophyll;
  iii. myoglobin, oxymyoglobin, and other hemeproteins;
  iv. water and fat soluble essential nutrients, minerals, and vitamins (e.g., riboflavin, vitamin A, vitamin D);
  v. food components containing fatty acids, particularly polyunsaturated fatty acids;
  vi. oils (e.g., soybean oil);
  vii. proteins (e.g., proteins derived from the amino acids tryptophan, histidine, tyrosine, methionine, cysteine, etc.);
  viii. pharmaceutical compounds;
  ix. personal care and cosmetic formulation compounds and their components;
  x. household chemicals and their components; and
  xi. agricultural chemicals and their components.

The species of interest could be studied in neat form or as a component of a solution or formulation. In certain embodiments, multiple photosensitive entities could be present, each at different concentrations. Different modes of light-induced change or degradation could occur in the system based upon the chemical nature of the photosensitive entities present to participate in the changes. For complete food systems, a combination of fats, oxygen, and photosensitive nutrients could be present to allow the interplay between multiple photosensitive entities and associated species to be observed upon light exposure. To allow for targeted and focused study as well as ease of analysis, model systems could be employed where only a single or a few components are included such that effects are isolated to a lesser number of components. Within a model system, a combination of entities that interact with light via different mechanisms could allow for a multi-dimensional assessment of light protection performance via a single experiment without the complexities of the study of a complete food system. Entities that interact with light via pathways that involve singlet oxygen represent one class of photosensitive entities. Such a list is disclosed by Min et al. (Min, D. B. and Boff, J. M.; Chemistry and Reaction of Singlet Oxygen in Foods. *CRFSFS.* 2002, 1, 58-72). Other entities that themselves are photosensitizers (e.g., riboflavin), may allow for a different learning regarding light protection performance. In another embodiment, combinations of entities could be used to affect the rate of the changes occurring to the entities, for example the inclusion of a photosensitizer may accelerate the effect while the inclusion of an antioxidant may retard the effect. Thus, in certain embodiments, a single photosensitive entity could be present in the sample cell, while, in other embodiments, at least 2, 3, 4, 5, 6, 7, 8, 9, 10, 11, 12, 13, 14, 15, or more photosensitive entities can be simultaneously present and/or studied. In particular embodiments, the photosensitive entities present and/or studied include one or more photosensitive entities from 2, 3, 4, 5, 6, 7, 8, 9, 10 or all 11 of each of the following classes:
  i. natural and synthetic food additives, dyes, and pigments (e.g., curcumin, erythrosine);
  ii. chlorophyll;
  iii. myoglobin, oxymyoglobin, and other hemeproteins;
  iv. water and fat soluble essential nutrients, minerals, and vitamins (e.g., riboflavin, vitamin A, vitamin D);

v. food components containing fatty acids, particularly polyunsaturated fatty acids;
vi. oils (e.g., soybean oil);
vii. proteins (e.g., proteins derived from the amino acids tryptophan, histidine, tyrosine, methionine, cysteine, etc.);
viii. pharmaceutical compounds;
ix. personal care and cosmetic formulation compounds and their components;
x. household chemicals and their components; and
xi. agricultural chemicals and their components.

In particular embodiments, the photosensitive entities studied include one or more photosensitive entities from class i and ii, class i and iii, class i and iv, class i and v, class i and vi, class i and vii, class i and viii, class i and ix, class i and x, class i and xi, class ii and iii, class ii and iv, class ii and v, class ii and vi, class ii and vii, class ii and viii, class ii and ix, class ii and x, class ii and xi, class iii and iv, class iii and v, class iii and vi, class iii and vii, class iii and viii, class iii and ix, class iii and x, class iii and xi, class iv and v, class iv and vi, class iv and vii, class iv and viii, class iv and ix, class iv and x, class iv and xi, class v and vi, class v and vii, class v and viii, class v and ix, class v and x, class v and xi, class vi and vii, class vi and viii, class vi and ix, class vi and x, class vi and xi, class vi and viii, class vii and ix, class vii and x, class vii and xi, class viii and ix, class viii and x, class viii and xi, class ix and x, class ix and xi, class x and xi, or any combination thereof.

Each photosensitive entity can be present at a concentration of, for example, 0.0000001 wt % to 100 wt %. In certain embodiments, the photosensitive entity is present at a concentration of at least about 0.0000001 wt %, 0.000001 wt %, 0.00001 wt %, 0.0001 wt %, 0.001 wt %, 0.01 wt %, 0.01 wt %, 0.1 wt %, 1.0 wt %, 2.0 wt %, 3.0 wt %, 4.0 wt %, 5.0 wt %, 10.0 wt %, 20.0 wt %, 30.0 wt %, 40.0 wt %, 50.0 wt %, 60.0 wt %, 70.0 wt %, 80.0 wt %, 90.0 wt %, 95.0 wt %, 99.0 wt %, or 100.0 wt %. In certain embodiments, the photosensitive entity is present at a concentration of less than about 100.0 wt %, 99.0 wt %, 95.0 wt %, 90.0 wt %, 80.0 wt %, 70.0 wt %, 60.0 wt %, 50.0 wt %, 40.0 wt %, 30.0 wt %, 20.0 wt %, 10.0 wt %, 5.0 wt %, 4.0 wt %, 3.0 wt %, 2.0 wt %, 1.0 wt %, 0.1 wt %, 0.01 wt %, 0.001 wt %, 0.0001 wt %, 0.00001 wt %, 0.000001 wt %, or 0.0000001 wt %. The concentrations are dependent upon the species under evaluation and its typical concentration during practical applications and uses.

The sample cell and sample contained therein are brought to an appropriate temperature for the test, for example a temperature between about −20° C. and about 100° C. Light produced by the light source, which has been optionally collimated, filtered, focused, and/or sized, at a desired intensity (e.g., 0.01-5 W/cm$^2$) and wavelength (e.g., 290-1000 nm) is then made to impinge upon the test material. The light that passes through the test material in turn impinges upon sample cell 44 and the sample contained therein.

Because the entity within the sample cell is photosensitive, the light impinging upon the sample will cause some level of change to the entity. At desired intervals, a test aliquot is removed from the sample cell 44. The test aliquots are then examined for the presence of the photosensitive molecule(s) or derivative product(s) thereof such that the amount of change can be quantified. Suitable analytical methods for determining the amount of light-induced change or degradation include HPLC (high performance liquid chromatography), GC (gas chromatography), IR (infrared) spectroscopy, NMR (nuclear magnetic resonance) spectroscopy, UV-VIS (ultra-violet, visible) spectroscopy, MS (mass spectrometry) coupled with other techniques (e.g., GC-MS and LC-MS), fluorescence spectroscopy, ion chromatography, thin layer chromatography (TLC), analytical wet chemistry, and/or electrochemical analysis (e.g., polarography, voltammetry). In particular embodiments, the analytical method is HPLC (high performance liquid chromatography) or GC (gas chromatography).

The experiment is continued for the desired length of time, with samples taken at the desired intervals. The run time is a function of the nature of the photosensitive entity, environmental conditions (e.g., temperature and gas modification), and the analytical study of its associated rate of change. In certain embodiments, the experimental run time is less than 12 hours, less than 11 hours, less than 10 hours, less than 9 hours, less than 8 hours, less than 7 hours, less than 6 hours, less than 5 hours, less than 4 hours, less than 3 hours, less than 2 hours, less than 1 hour, less than 45 minutes, or less than 30 minutes.

The sampling intervals should be selected to obtain a minimum of three data points. In particular embodiments, the sampling intervals are selected to obtain at least 4, 5, 6, 7, 8, 9, 10, 11, 12, 13, 14, 15, 16, 17, 18, 19, 20, 25, 30, 35, 40, 45, or 50 data points. In certain embodiments the data points are evenly distributed or nearly-evenly distributed throughout the entire duration of the run time. Selected intervals will be dependent upon the rate of change of the photosensitive entities. In certain embodiments, the samples are extracted automatically via syringe pump or other suitable device and delivered directly to analytical equipment for analysis.

Once all samples have been collected and analyzed from an experimental run, the resulting data points tracking the change of the photosensitive molecule(s) or derivative product(s) can be used to assign a photoprotective performance value to the test material. Such photoprotective values can include, for instance, a pseudo-first order rate constant for light-induced change or degradation of the photosensitive entity being examined. Moreover, by regulating the variables of the experimental runs, such as light spectra, light intensity, light focus, duration of light exposure, sample temperature, sample homogeneity, and sample atmospheric conditions, results can be obtained with sufficient accuracy and precision to allow for quality run-to-run comparisons to be made.

In certain other embodiments, numerous test materials with one or more known quantitative or qualitative properties can be evaluated and a photoprotective performance value assigned to each such test material. The known quantitative or qualitative property can be, for example, a known concentration of opacifying agent (e.g., $TiO_2$) or a known reflectivity or opacity value (e.g., a TAPPI opacity value). In certain examples, the known quantitative or qualitative property or properties utilized in the predictive model include one or more of the following: whiteness index ASTM E313; brightness index ASTM D985; CIE L*a*b* tri-stimulus data ASTM designation of E313-10, D2244, E 1347, E1349, E1477, E2214, E284, E308, E805, E991, E1331, E275, D2616, D2745, D3134, D3964, D4877, D6290; DuPont Appearance Analyzer data; Diffuse Brightness of Paper and Paperboard (d/0) ASTM D2470; Standard test for haze for plastics ASTM D1003; Brightness, Directional (TAPPI) (T452); Brightness Directional; Brightness, Diffuse (T525); Brightness with Color (Diffuse (Micro TB1C) or Directional/TAPPI (MicroS-5)); Printing & calculated TAPPI Opacity, Scattering & Absorption Coefficients, Sheet Brightness (T519); Directional/TAPPI Opacity, Scattering Coefficient, Absorption Coefficient (T425); T/dyne Micro TB-1C: Diffuse brightness, opacity, color, color difference, ASTM Index, & tristimulus; T/dyne Micro S-5 BOC:Dir/TAPPI brightness, opacity, color, color difference, ASTM Index, & tristimulus; Color, Hunter or CIE L*A*B* (State Directional or Diffuse Values), opacifying agent composition(s), and/or opacifying agent(s) loading. Where a correlative behavior is observed and modeled, the photoprotective performance values of these known materials can then be used to confidently assign a predicted photoprotective performance value to a material of the same class that has not been evaluated using the apparatus of the present invention, but that does have a known value for the quantitative or qualitative parameter included in the model. For instance, several test materials with known TAPPI opacity values and/or known $TiO_2$ concentrations could be evaluated using the apparatus and methods disclosed herein, and a photoprotective performance value assigned to each. The photoprotective performance values and TAPPI opacity or $TiO_2$ concentration values of these materials can in turn be used to generate a metric or predictive model that predicts the photoprotective performance value of a material based upon its TAPPI opacity and or $TiO_2$ concentration. This metric or model can then be used to predict the photoprotective performance vale of an untested material of the same class with a known TAPPI Opacity or $TiO_2$ content.

EXAMPLES

Example 1

The ANOVA Gage Repeatability and Reproducibility (R&R) measurement systems analysis methodology employs an analysis of variance (ANOVA) random effects model to understand the measurement system capability. In a Gage R&R study, the amount of variability observed in measurements by the measurement system is compared to the total variability observed. Gage R&R study methodologies were applied to assess the repeatability and reproducibility of the device of FIG. 1 used with the method disclosed herein. This study was designed and analyzed using Minitab software.

The Gage R&R study involved replicate evaluation of each of five film samples, or parts, by two different operators. These twenty separate experiments were conducted in random order within operators.

In this Gage R&R study, the following method conditions were fixed:
Photosensitive Entity: Riboflavin dissolved in pH 6.4 aqueous phosphate buffer solution at a target concentration of 30.5±1.5 mg/L
Temperature: 4±1° C.
Atmosphere: Air
Light Power Density: 0.375±0.005 $W/cm^2$
Sampling Times: samples withdrawn after 0, 10, 40, 80, 120, 160, and 200 minutes of light exposure
Photosensitive Entity Analysis Method: HPLC The test materials used for the study consisted of titanium dioxide pigmented low density polyethylene (LDPE) films prepared by cast film extrusion of approximately 48 μm in thickness. Film swatches of about 6 cm by 13 cm were cut from a larger film sample for study. Each swatch was evaluated with light exposure only once. After evaluation, each swatch was set aside for additional measurements including replicate measures of TAPPI opacity and film thickness where average values are reported.

Figure 5:
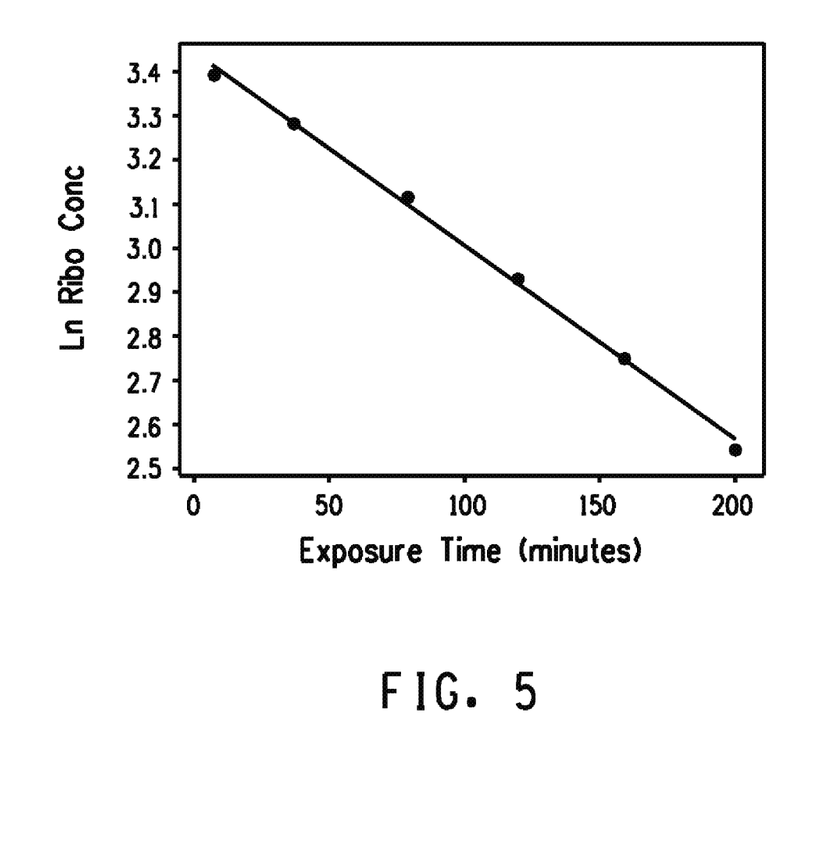
FIG. 5 illustrates a plot of the natural log of riboflavin concentration versus light exposure time for one exemplary test material experiment.

The output of each run was the pseudo-first order rate constant of riboflavin decomposition. The decomposition of riboflavin in dilute aqueous solution under ambient atmosphere (i.e., excess of $O_2$ available for reaction as a dissolved gas in the solution) has been shown to follow pseudo-first order rate kinetics when said solution is exposed to UV or visible light (e.g., Ahmad, I.; Fasihullah, Q.; Noor, A; Ansari, I. A.; Ali, Q. Nawab Manzar, International Journal of Pharmaceutics (2004), 280(1-2), 199-208). More specifically, under conditions during which the energy distribution of light that is incident upon said solution is held constant, said decomposition can be described by the following integrated rate expression:

$$Ln[Riboflavin]_t = (-k' \times t) + Ln[Riboflavin]_0$$

where:
$[Riboflavin]_t$ = Riboflavin concentration at time=t
$[Riboflavin]_0$ = Initial riboflavin concentration prior to light exposure
t = Light exposure time
k' = Pseudo-first order rate constant When such reaction kinetics are observed, a plot of $Ln[Riboflavin]_t$ versus exposure time yields a straight line, the slope of which is the desired pseudo-first order rate constant. For this work, the rate constant plot was constructed using Minitab software, and the desired slope data was extracted using the Minitab 'Fitted Line Plot' analysis tool. The correlation coefficient ($R^2$) values indicating the quality of the linear fit derived from the linear regression analyses were all 98.5% or greater, showing excellent agreement of the data to the linear model. A sample of these data is shown in FIG. 5 and the complete set of reduced data from each of the plots generated as such is presented in Table 1.

TABLE 1

| | | | Gage R&R Data | | |
|---|---|---|---|---|---|
| Run Order | Test Material | Operator | Rate Constant $(min^{-1})$ | Average TAPPI Opacity (%) | Average Film Thickness (in) |
| 1 | O1 | 1 | 0.0180 | 28.04 | 0.00188 |
| 2 | O4 | 1 | 0.0029 | 66.47 | 0.00185 |
| 3 | O5 | 1 | 0.0018 | 78.82 | 0.00189 |
| 4 | O2 | 1 | 0.0087 | 39.87 | 0.00186 |
| 5 | O3 | 1 | 0.0047 | 52.88 | 0.00183 |
| 6 | O1 | 2 | 0.0195 | 28.17 | 0.00184 |
| 7 | O5 | 2 | 0.0016 | 78.71 | 0.00204 |
| 8 | O4 | 2 | 0.0029 | 66.28 | 0.00190 |
| 9 | O3 | 2 | 0.0045 | 52.17 | 0.00188 |
| 10 | O2 | 2 | 0.0084 | 39.88 | 0.00190 |
| 11 | O1 | 1 | 0.0199 | 28.22 | 0.00188 |
| 12 | O5 | 1 | 0.0020 | 79.11 | 0.00196 |
| 13 | O4 | 1 | 0.0035 | 65.55 | 0.00184 |
| 14 | O2 | 1 | 0.0098 | 39.20 | 0.00183 |
| 15 | O3 | 1 | 0.0047 | 53.10 | 0.00193 |
| 16 | O1 | 2 | 0.0196 | 28.42 | 0.00189 |
| 17 | O3 | 2 | 0.0050 | 52.77 | 0.00190 |
| 18 | O5 | 2 | 0.0019 | 79.20 | 0.00193 |
| 19 | O4 | 2 | 0.0031 | 66.02 | 0.00193 |
| 20 | O2 | 2 | 0.0084 | 40.08 | 0.00191 |

The Gage R&R ANOVA analysis was conducted on the data presented in Table 1. The analysis outputs are shown in Table 2. This analysis revealed that 0.58% of the total contribution and 7.6% of the total study variability can be attributed to the measurement system with the remainder due to inherent (and by design) part-to-part variations. With a 95% confidence level for the data interpretation, neither operator-to-operator differences nor operator-part interactions were observed in this study (Operator ANOVA 'p' value=0.661 with operator-part interactions included; Operator*part ANOVA 'p' value=0.445). Thus, this study demonstrated that the measurement system is capable of producing reproducible and repeatable data.

TABLE 2

Minitab Analysis Outputs of the ANOVA
Analysis of the Gage R&R Study

| Source | VarComp | % Contribution (of VarComp) |
|---|---|---|
| Total Gage R&R | 0.0000003 | 0.58 |
| Repeatability | 0.0000003 | 0.58 |
| Reproducibility | 0.0000000 | 0.00 |
| Operators | 0.0000000 | 0.00 |
| Part-To-Part | 0.0000496 | 99.42 |
| Total Variation | 0.0000499 | 100.00 |

| Source | Study Var StdDev (SD) | Study Var (6 * SD) | % Study Var (% SV) |
|---|---|---|---|
| Total Gage R&R | 0.0005382 | 0.0032292 | 7.62 |
| Repeatability | 0.0005382 | 0.0032292 | 7.62 |
| Reproducibility | 0.0000000 | 0.0000000 | 0.00 |
| Operators | 0.0000000 | 0.0000000 | 0.00 |
| Part-To-Part | 0.0070455 | 0.0422727 | 99.71 |
| Total Variation | 0.0070660 | 0.0423959 | 100.00 |

Number of Distinct Categories = 18

The Gage R&R results thus suggest that the measurement system will yield riboflavin degradation rate constant data of adequate quality. This conclusion can be reasonably extended to other riboflavin based exposure studies that involve reasonable deviations away from the exposure conditions utilized in this Gage R&R study. Examples of such deviations include modifications to the following: the light power density and/or spectral distribution that are incident upon the light attenuating test material, the riboflavin solution temperature, the initial riboflavin solution concentration and the test material composition. Additional extensions include other (i.e., non-riboflavin) photosensitive entities that may or may not exhibit pseudo-first order light-induced change or degradation rate kinetics and that may or may not be dissolved in water.

Example 2

The rate constant data from Example 1 are analyzed along with additional characterization of the film swatches. The rate constant data in Table 1 are plotted in FIG. 6 along with a fitted data model. This data model was fitted to the data points to yield a photoprotective model as a function of TAPPI Opacity.

Figure 6:
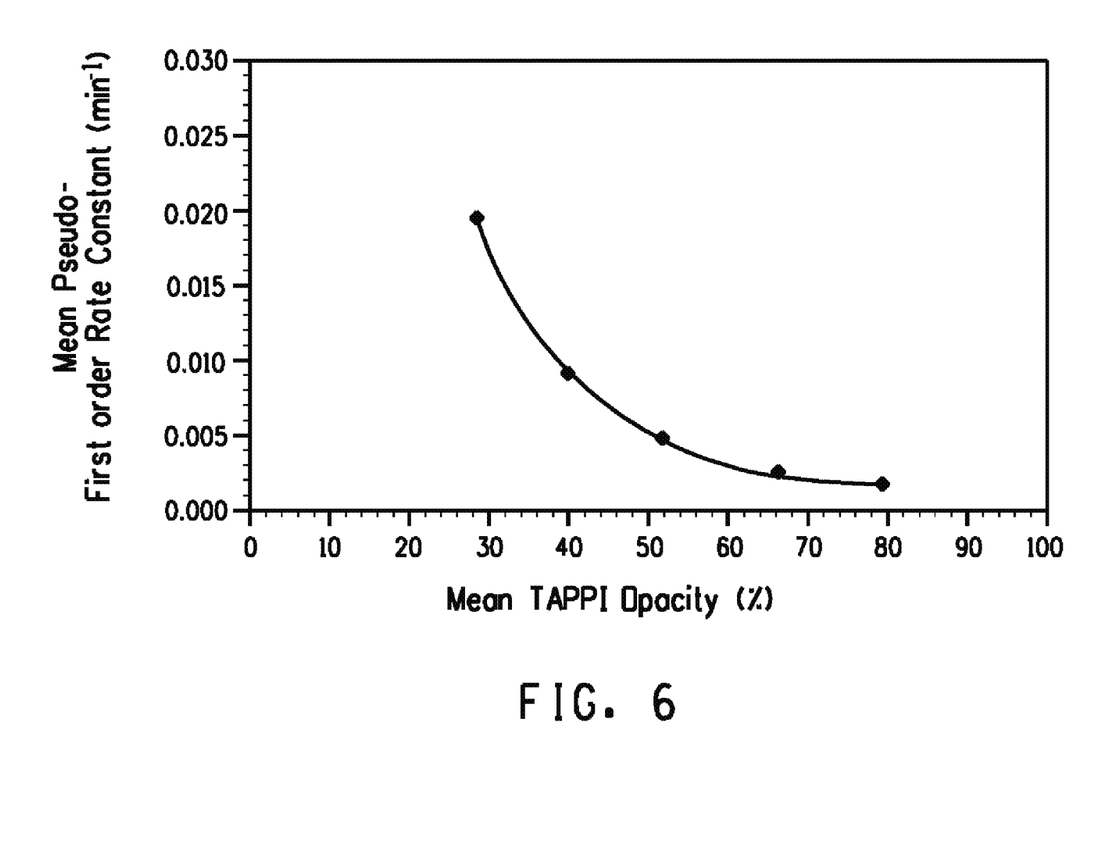
FIG. 6 illustrates a plot of mean pseudo-first order rate constant versus mean TAPPI opacity for one exemplary test material experiment.

This plot and model demonstrate that the light protection performance (i.e., the ability to protect riboflavin from light-induced degradation) of the titanium dioxide loaded LDPE films utilized in this study can indeed be linked to the TAPPI Opacity values of said films, a relationship that is well described by a power law model. This demonstrates that for this type of material that TAPPI Opacity can be used to predict light protection performance. This method could be applied to other materials.

These type of data can in turn be used in the method of the present invention to confidently predict the light protection performance for test material comprised of the same or comparable titanium dioxide and LDPE materials in different relative amounts with a known TAPPI opacity.

Example 3

The same method conditions were utilized as in Example 1, but the evaluated samples were two pieces (each evaluated in duplicate) derived from the same titanium dioxide pigmented, high density polyethylene (HDPE) bottle (1.8 wt % titanium dioxide, 1380 μm wall thickness, 97.9% TAPPI Opacity) and HPLC analysis was performed after 0, 10, 25, 50, 75, 100, and 125 minutes of light exposure. The $R^2$ values obtained from the linear regression analyses were all 98.5% or greater and a mean pseudo-first order rate constant of 0.000691 $min^{-1}$ for riboflavin decomposition was found.

Example 4

The same method conditions were utilized as in Example 3, but the evaluated samples consisted of film swatches (four in total, each evaluated once) derived from the same piece of titanium dioxide pigmented, low density polyethylene film (1.0 wt % titanium dioxide, 47 μm thick, 39% TAPPI Opacity) and two of the swatches were evaluated at 14±1° C. The $R^2$ values obtained from the linear regression analyses were all 99.3% or greater and the 4° C. and 14° C. mean pseudo-first order rate constants were found to be 0.0112 $min^{-1}$ and 0.0154 $min^{-1}$, respectively, indicating the sensitivity of temperature on the riboflavin degradation kinetics as consistent with the theoretical predictions given by the Arrhenius equation.

Example 5

The same method conditions were utilized as in Example 3, but the evaluated samples consisted of film swatches (four in total, each evaluated once) derived from the same piece of titanium dioxide pigmented, low density polyethylene film (1.0 wt % titanium dioxide, 47 μm thick, 40% TAPPI Opacity) and two of the swatches were evaluated using a UV light filter attenuated light beam (essentially complete wavelength cutoff at 385 nm and below), said beam possessing a light power density of 0.287 $W/cm^2$. The $R^2$ values obtained from the linear regression analyses were all 99.3% or greater and the mean pseudo-first order rate constants with and without the UV light attenuating filter in the light beam were found to be 0.0062 $min^{-1}$ and 0.0112 $min^{-1}$, respectively, indicating the sensitivity of riboflavin degradation kinetics to the presence of UV light.

Example 6

The same method conditions were utilized as in Example 3, but the evaluated samples consisted of film swatches (four in total, each evaluated once) derived from the same piece of titanium dioxide pigmented, low density polyethylene film (1.0 wt % titanium dioxide, 47 μm thick, 40% TAPPI Opacity) and two of said swatches were evaluated using a reduced light power density of 0.201 $W/cm^2$. The $R^2$ values obtained from the linear regression analyses were all 99.3% or greater and the mean pseudo-first order rate constants for light power densities of 0.375 $W/cm^2$ and 0.201 $W/cm^2$ were found to be 0.0112 $min^{-1}$ and 0.0045 $min^{-1}$, respectively, indicating the sensitivity of riboflavin degradation kinetics to light power density.

Example 7

The light protection performance of an untested material of known TAPPI opacity within the same class of materials of that used to construct the photoprotective model of Example 2 (FIG. 6) is predicted using said model. The TAPPI opacity of the untested material was measured to be 35.95%. The model predicts a k' value 0.0112 $min^{-1}$. The k' value of the untested material was measured to be 0.0111 min$^{-1}$ using the method of Example 1 with the HPLC analyses performed after 0, 10, 25, 50, 75, 100, and 125 minutes of light exposure. These results demonstrate that the photoprotective model is useful for the prediction of light protection performance based upon TAPPI opacity.

What is claimed is:

1. A device for quantifying the photoprotective performance of a material, the device comprising:
   (a) a sample supply and control apparatus comprising:
   (I) a cell having controlled optical properties, the cell capable of containing a sample comprising one or more photosensitive entities;
   (II) a sample temperature sensor for monitoring the temperature of the sample within the cell;
   (III) a temperature control for maintaining the cell at a specified temperature between about −20° C. and about 100° C.;
   (IV) a dry air supply for delivering low-humidity air to one or more exposed surfaces of the cell; and
   (V) an agitator for maintaining sample homogeneity within the cell;
   (b) a light generation and control apparatus comprising:
   (I) a light source, wherein the light source generates a light beam with a spectral signature between about 290 and about 1000 nm and an intensity between about 0.01 and about 5 W/cm$^2$;
   (II) a light beam collimating lens;
   (III) an infrared filter;
   (IV) a shutter; and
   (V) an iris; and
   (c) a test material holder positioned between the light generation and control apparatus and the sample supply and control apparatus such that, when a test material is placed in the test material holder, the light beam impinges upon the test material and any penetrating light impinges upon the cell.

2. The device of claim 1, wherein the sample supply and control apparatus further comprises an atmosphere control and monitoring apparatus within the cell, wherein the atmosphere control and monitoring apparatus comprises a gas supply device, an oxygen sensor, and the means to close the cell to contain and maintain the modified atmosphere.

3. The device of claim 1, wherein the light generation and control apparatus further comprises a spectral filter.

4. The device of claim 1 wherein the light source generates an intensity between about 0.05 and 5 W/cm$^2$.

5. The device of claim 1 wherein the light source generates an intensity between about 0.05 and 1 W/cm$^2$.

6. The device of claim 1 wherein the light source generates an intensity between about 0.1 and 5 W/cm$^2$.

7. The device of claim 1 wherein the light source generates an intensity between about 0.1 and 1 W/cm$^2$.

8. The device of claim 1 wherein the temperature control maintains the cell at the specified temperature between 1° C. and 50° C.

9. The device of claim 1 wherein the temperature control maintains the cell at the specified temperature between 1° C. and 25° C.

10. The device of claim 1 wherein the temperature control maintains the cell temperature to within ±1° C. of the temperature set point.

* * * * *